United States Patent
Wisselink

(10) Patent No.: US 6,428,565 B1
(45) Date of Patent: Aug. 6, 2002

(54) SYSTEM AND METHOD FOR EDOLUMINAL GRAFTING OF BIFURCATED OR BRANCHED VESSELS

(75) Inventor: Willem Wisselink, Dronton (NL)

(73) Assignee: Medtronic Ave, Inc., Santa Rosa, CA (US)

(*) Notice: Subject to any disclaimer, the term of this patent is extended or adjusted under 35 U.S.C. 154(b) by 0 days.

(21) Appl. No.: 09/412,861

(22) Filed: Oct. 5, 1999

Related U.S. Application Data

(62) Division of application No. 08/927,439, filed on Sep. 11, 1997, now Pat. No. 5,984,955.

(51) Int. Cl.⁷ .................................................. A61F 2/06
(52) U.S. Cl. ............................... 623/1.11; 623/1.23
(58) Field of Search ......................... 623/1.11, 1.23, 623/1.25, 1.32, 1.36, 1.35; 604/532

(56) References Cited

U.S. PATENT DOCUMENTS

| | | | | |
|---|---|---|---|---|
| 4,169,464 A | * | 10/1979 | Obrez | 604/532 |
| 4,577,631 A | | 3/1986 | Kreamer | |
| 4,935,017 A | * | 6/1990 | Sylvanowicz | 604/532 |
| 4,961,731 A | * | 10/1990 | Boydicky et al. | 604/532 |
| 4,983,166 A | * | 1/1991 | Yamawaki | 604/532 |
| 5,575,817 A | | 11/1996 | Martin | |
| 5,643,340 A | | 7/1997 | Nunokawa | |
| 5,653,743 A | * | 8/1997 | Martin | 623/1.35 |
| 5,676,697 A | | 10/1997 | McDonald | |
| 5,693,088 A | * | 12/1997 | Lazarus | 604/1.35 |
| 5,709,713 A | | 1/1998 | Evans et al. | |
| 5,755,770 A | | 5/1998 | Ravenscroft | |
| 5,902,088 A | * | 5/1999 | Martin | 604/532 |
| 5,961,548 A | * | 10/1999 | Shmulewitz | 623/1.35 |
| 5,984,955 A | * | 11/1999 | Wisselink | 623/1.35 |
| 6,033,434 A | * | 3/2000 | Borghi | 623/1.35 |
| 6,102,938 A | * | 8/2000 | Evans | 623/1.35 |
| 6,165,162 A | * | 12/2000 | Safar et al. | 604/532 |
| 6,165,214 A | * | 12/2000 | Lazarus | 623/1.35 |
| 6,251,133 B1 | * | 6/2001 | Richter et al. | 623/1.35 |

* cited by examiner

Primary Examiner—David H. Willse
Assistant Examiner—Suzette J. Jackson

(57) ABSTRACT

A system and method for endoluminal grafting of a main anatomical conduit (e.g., the aorta) and various branch conduits (e.g., side branch vessels such as the carotid, innominate, subclavian, intercostal, superior mesenteric, celiac, or renal arteries-or furcations such as the iliac arteries) which emanate from the main anatomical conduit. The grafting system generally comprises i) a primary graft having at least one opening therein and ii) at least one branch graft which is passable through the opening of the primary graft and into the branch conduit(s) such that the proximal end of each branch graft is in substantially fluid-tight sealing contact with the primary graft. Also disclosed is a specific system and method for grafting a bifurcated anatomical conduit (e.g., the aorto-iliac bifurcation) though only a single access opening (puncture site or incision) and a new balloon-anchorable guidewire system which is useable in the performance of such grafting of bifurcated anatomical conduits and numerous other medical procedures.

8 Claims, 6 Drawing Sheets

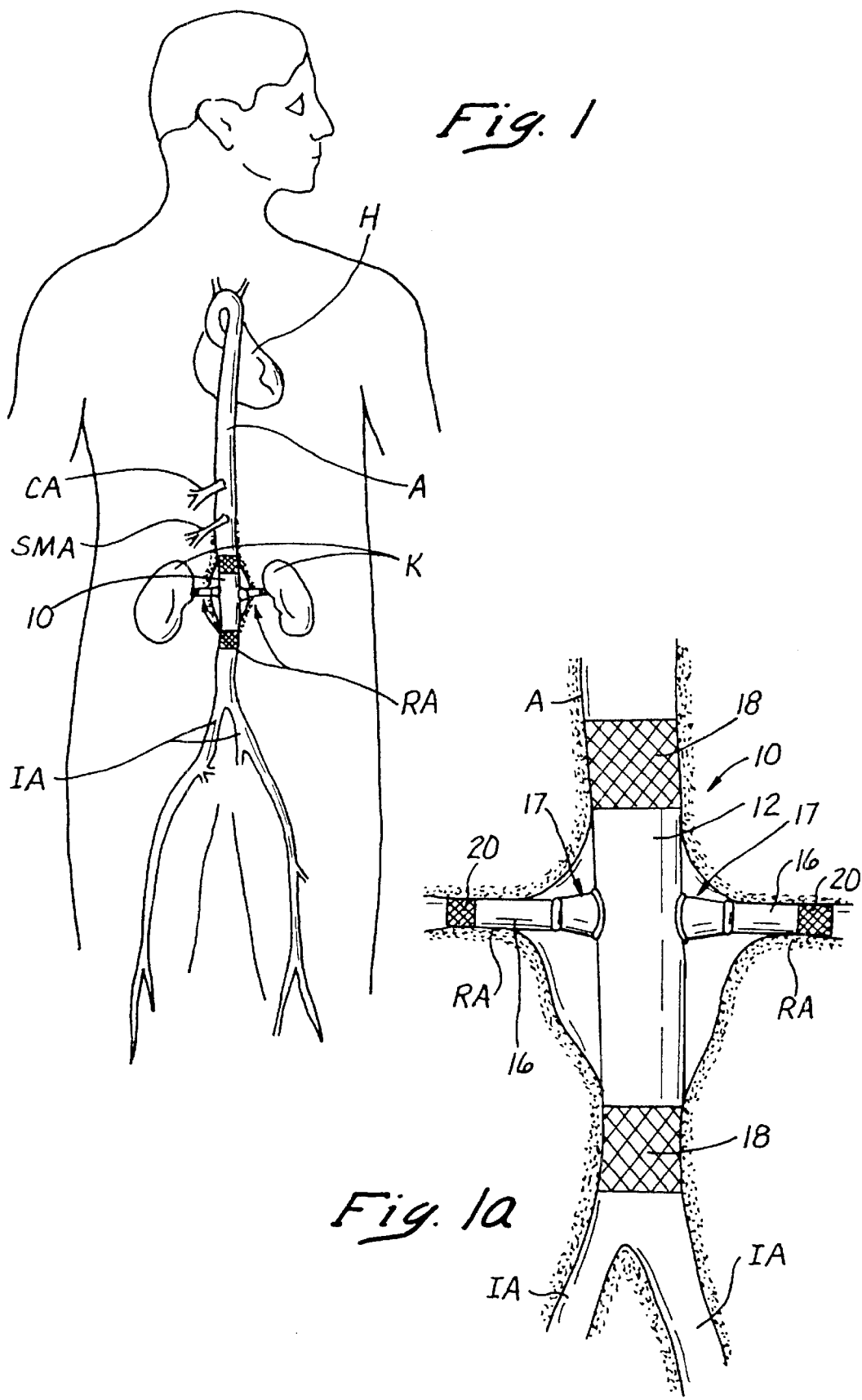

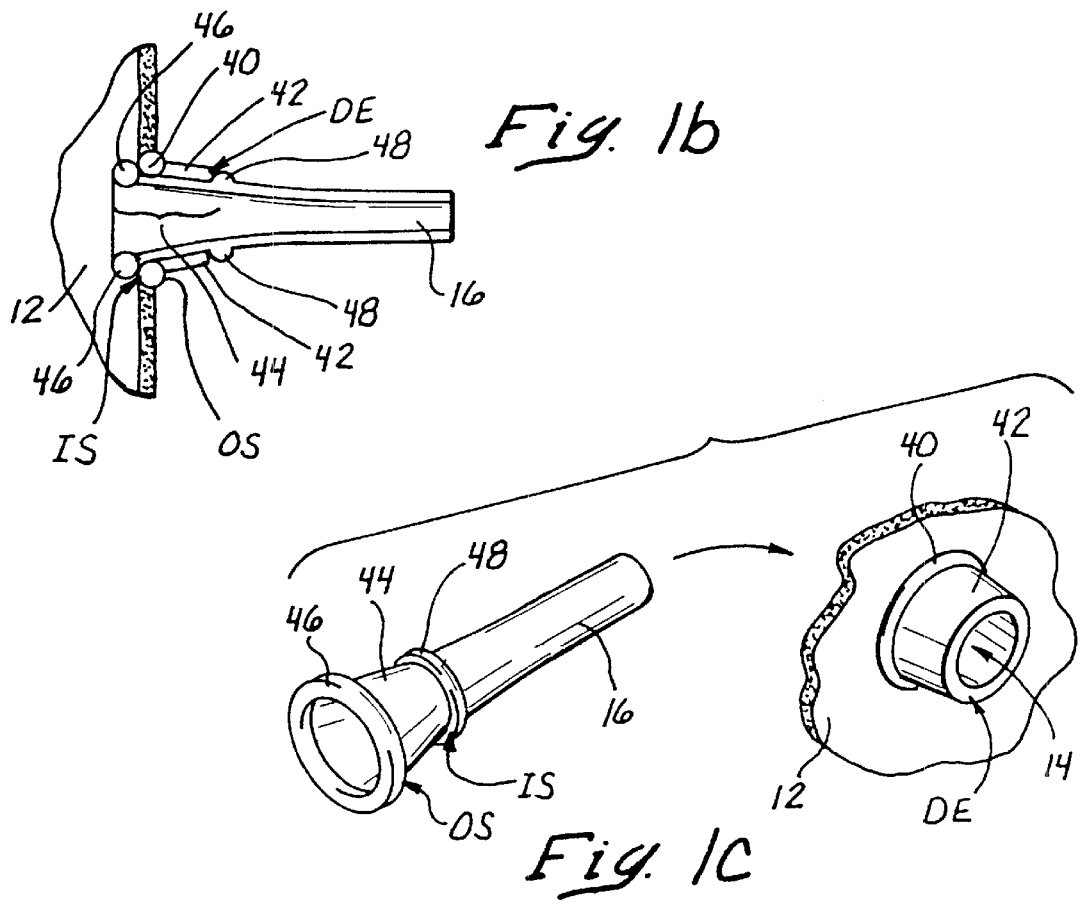
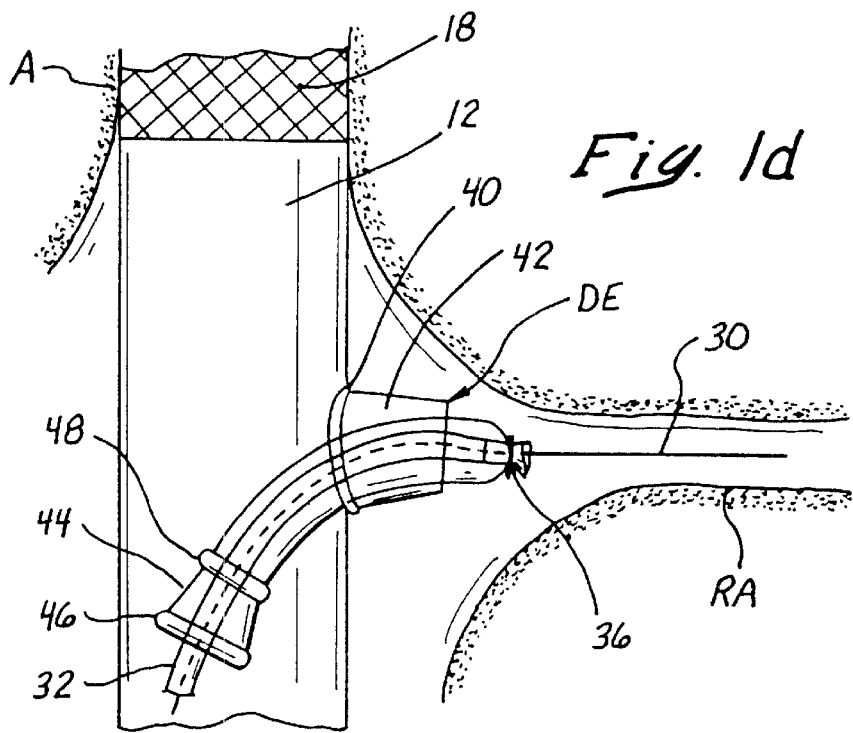

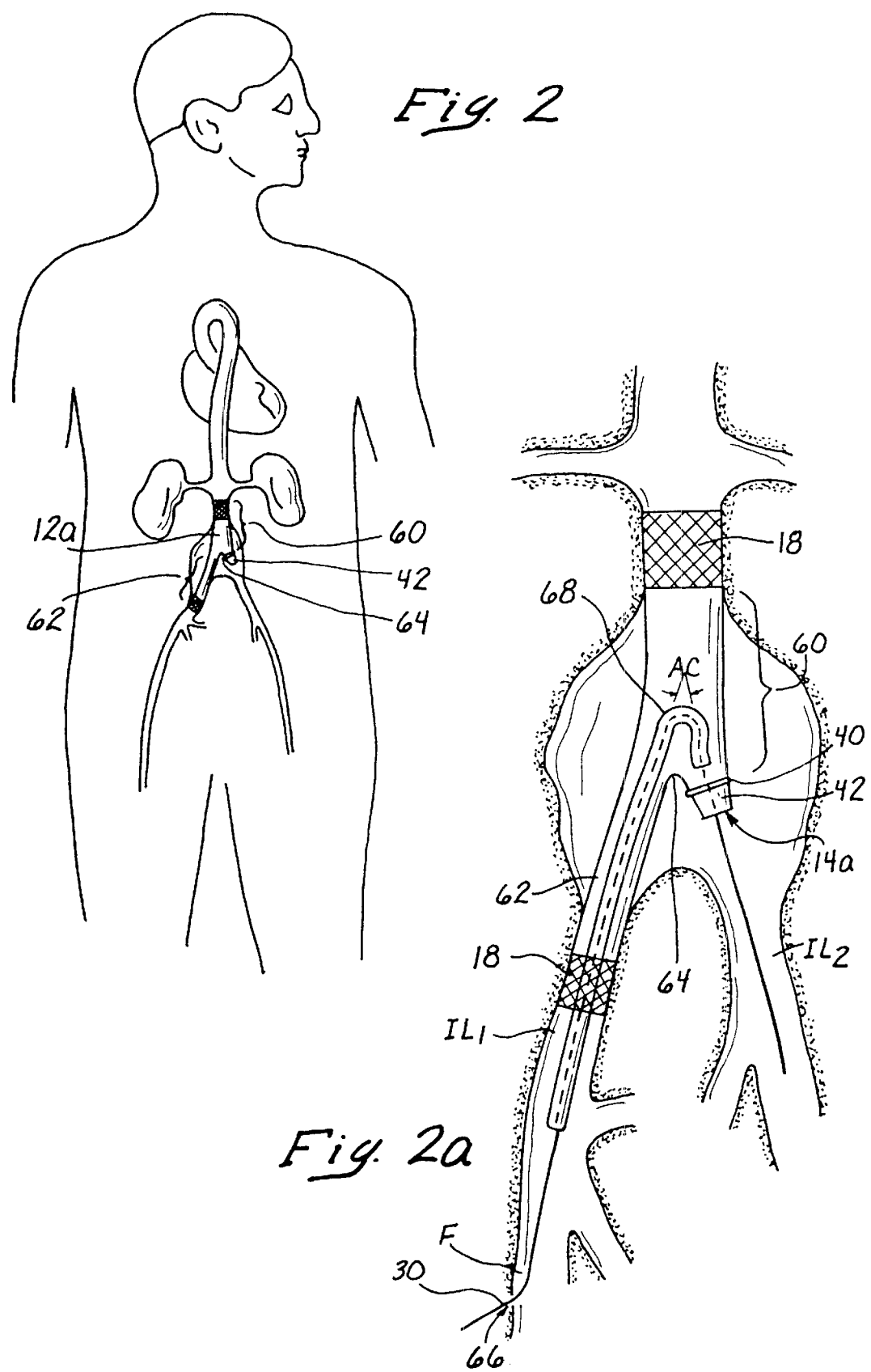

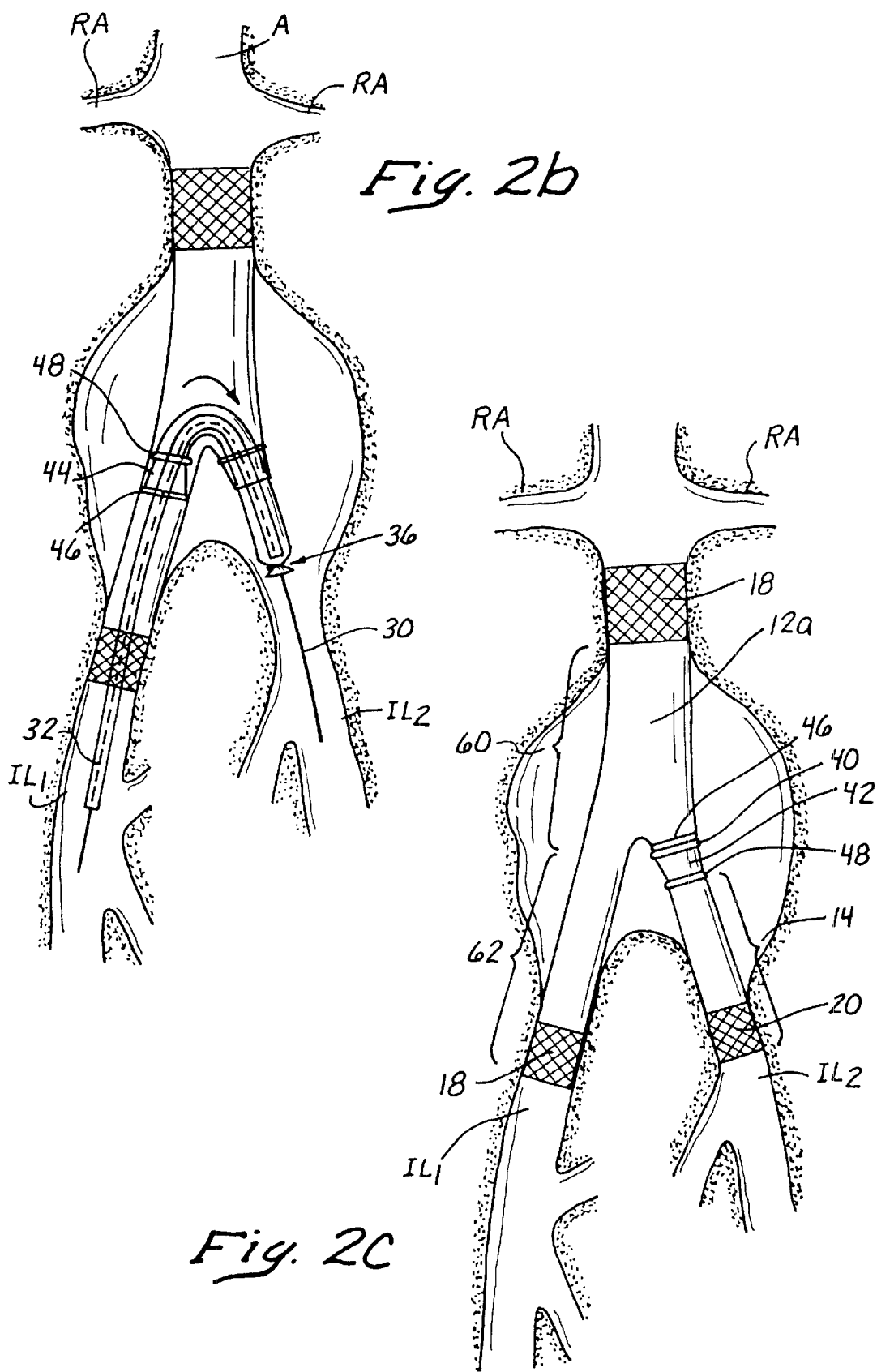

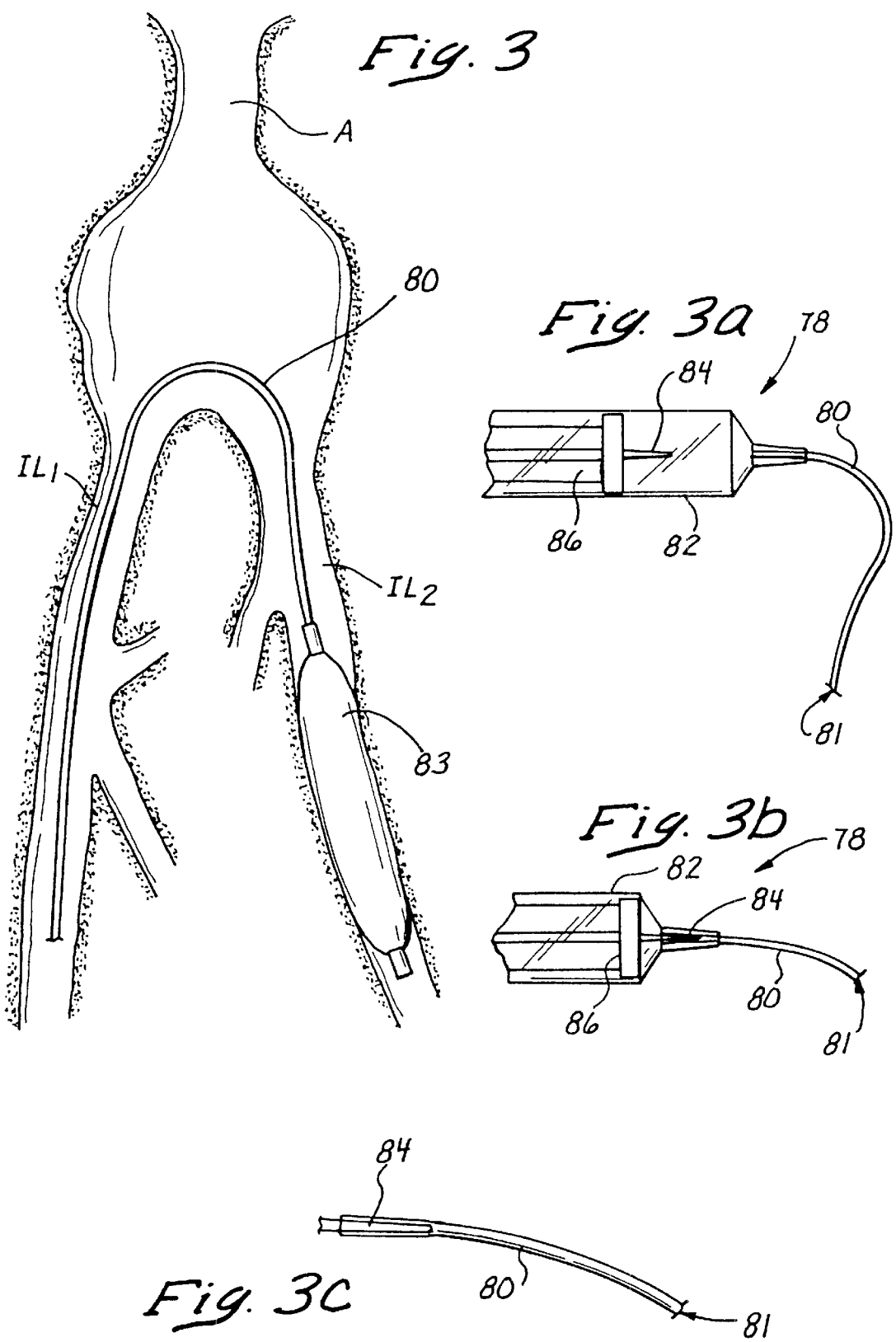

SYSTEM AND METHOD FOR EDOLUMINAL GRAFTING OF BIFURCATED OR BRANCHED VESSELS

This application is division of U.S. Ser. No 08/927,439 Sep. 11, 1997 U.S. Pat. No. 5,984,955.

FIELD OF THE INVENTION

The present invention relates generally to medical devices and methods, and more particularly to a system and method for endoluminal grafting of blood vessels or other tubular anatomical conduits which have furcations or side branches extending therefrom.

BACKGROUND OF THE INVENTION

Endoluminal grafting is a relatively noninvasive method for placing a tubular graft within the lumen of an anatomical conduit, such as a blood vessel. In certain cardiovascular applications of the technique, an endovascular graft may be implanted within an aneurysmic segment of a blood vessel (i.e., a blood vessel which has a region of localized dilatation wherein the blood vessel wall has become distended and weakened) to form a prosthetic flow conduit through the aneurysm, and to effectively isolate weakened portion of the blood vessel wall from the hemodynamic forces and pressures of the flowing blood.

The prior art has included numerous endovascular grafts of varying design. In general, these endovascular grafts typically comprise: a tube of pliable material (e.g., expanded polytetrafluoroethylene (ePTFE) or woven polyester) in combination with a graft anchoring component (e.g., a stent, a frame, a series of wire rings, hooks, barbs, clips, staples, etc.) which operates to hold the tubular graft in its intended position within the blood vessel. Most commonly, the graft anchoring component is formed of a radially expandable stent or frame which is either a) incorporated into the body of the tubular graft or b) formed separately from the graft and deployed within the graft lumen, and which is expandable to exert outwardly directed radial pressure against the surrounding blood vessel wall—thereby frictionally holding the graft in place. In operation, endovascular grafts which incorporate radially expandable graft anchoring devices are initially disposed in a radially collapsed configuration which is sufficiently compact to allow the graft to be transluminally advanced through the vasculature until it reaches the intended site of implantation. Thereafter, the graft (and the accompanying graft anchoring device) expands to a radially expanded configuration which is large enough to exert the desired outwardly-directed pressure against the blood vessel wall. In some embodiments, hooks, barbs, or other projections formed on the graft anchoring device, will insert into the wall of the blood vessel to ensure that the graft will be firmly held in its desired position, without slipping or migrating after implantation. These radially expandable graft anchoring devices are generally classifiable as either a.) self-expanding or b) pressure-expandable. Graft anchoring devices of the "self-expanding" are usually formed of a resilient material (e.g., spring metal) or shape memory alloy which automatically expands from a radially collapsed configuration to a radially expanded configuration, when relieved of surrounding constraint (e.g., a surrounding tubular sheath or catheter wall). On the other hand, those of the "pressure-expandable" variety are typically formed of malleable wire or other plastically deformable material which will deform to a radially expanded configuration in response to the exertion of outwardly directed pressure thereagainst— as by inflation of a balloon or actuation of another pressure-exerting apparatus which has been positioned within the graft anchoring device.

Endovascular grafting is a clinically viable alternative to traditional surgery in patients who suffer from aneurysms of the aorta. Indeed, may patients who are diagnosed with aortic aneurysms are in relatively poor health, and may be characterized as poor surgical risks. Moreover, the traditional surgical approach to repair of aortic aneurysms requires cross-clamping of the aorta above the aneurysm, which can result in ischemic damage to organs or other untoward results. Nonetheless, if allowed to remain untreated, a substantial percentage of aortic aneurysms may ultimately dissect or rupture, with catastrophic consequences. Thus, endovascular grafting offers a potential means for repair of aortic aneurysms, without the risks and potential complications of traditional aneurysm repair surgery.

Depending on which region(s) of the aorta is/are involved, the aneurysm may extend into areas of bifurcation (i.e., the inferior end of the aorta where it bifurcates into the iliac arteries) or segments of the aorta from which smaller "branch" arteries extend. In this regard, the various types of aortic aneurysms may be classified on the basis of the region(s) of aneurysmic involvement, as follows:

A. Thoracic Aortic Aneurysms:
  Aneurysms involving the ascending thoracic aorta
  Aneurysms involving the aortic arch and branch arteries which emanate therefrom (i. e., the subclavian arteries)

B. Thoracoabdominal Aortic Aneurysms:
  Aneurysms involving the descending thoracic aorta and branch arteries which emanate therefrom (i.e., thoracac intercostal arteries) and/or the suprarenal abdominal aorta and branch arteries which emanate therefrom (i.e., renal, superior mesenteric, celiac and/or intercostal arteries).

C. Abdominal Aortic Aneurysms:
  Aneurysms involving the pararenal aorta and the branch arteries which emanate therefrom (i.e., the renal arteries)
  Anneurysms involving the infrarenal aorta with or without illiac involvement Unfortunately, not all patients diagnosed with aortic aneurysm are presently considered to be candidates for endovascular grafting. This is largely due to the fact that most of the endovascular grafting systems of the prior art are not designed for use in regions of the aorta from which side branches (i.e., carotid, innominate, subclavian, intercostal, superior mesenteric, celiac or renal arteries) extend. In fact, most of the clinical experience with endoaortic grafting has been for the treatment of infrarenal aneurysms, with or without illiac involvement. Examples of endovascular grafting methods and systems useable to treat such infrarenal anneurysms include those described in the following U.S. Pat. No. 4,577,631 (Kreamer); U.S. Pat. No. 5,211,658 (Clouse); U.S. Pat. No. 5,219,355 (Parodi et al.); U.S. Pat. No. 5,316,023 (Palmaz et al.); U.S. Pat. No. 5,360,443 (Barone et al.); U.S. Pat. No. 5,425,765 (Tifenbrun et al.); U.S. Pat. No. 5,609,625; (Piplani et al.); U.S. Pat. No. 5,591,229 (Parodi et al.); U.S. Pat. No. 5,578,071 (Parodi); U.S. Pat. No. 5,571,173 (Parodi); U.S. Pat. No. 5,562,728 (Lazarus et al.); U.S. Pat. No. 5,562,726 (Chuter); U.S. Pat. No. 5,562,724 (Vorwerk et al.); U.S. Pat. No. 5,522,880 (Barone et al.); and U.S. Pat. No. 5,507,769 (Marin et al.).

Most if not all of the endovascular grafts which have been designed for use in treating infrarenal aneurysms require that a proximal "neck" (e.g., at least two (2) centimeters of non-aneurysmic aorta) exist inferior to the renal arteries, in order to provide a region where the superior end of the graft may be securely anchored in place, without blocking or restricting blood flow into the renal arteries. The deployment of endovascular grafts within regions of the aorta from which branch arteries extend (e.g., regions of the aorta from which the renal, superior mesenteric, celiac, intercostal, and/or subclavian arteries emanate) present additional technical challenges because, in those cases, the endovascular graft must be designed, implanted and maintained in a manner which does not impair the flow of blood into the branch arteries.

U.S. Pat. No. 5,425,765 (Tifenbrun et al.) has described an endovascular graft which has one or more openings or fenestrations formed at specific locations, to allow blood to flow from the aorta into one or more branch arteries. However, such fenestrations do not form discrete conduit(s) through which blood is channeled into each branch artery. As a result, the area surrounding the fenestrations could be prone to i) the leakage of blood into the space between the outer surface of the aortic graft and the surrounding aortic wall or ii) post-implantation migration or movement of the graft causing misalignment of the fenestration(s) and the branch artery(ies)—with resultant impairment of flow into the branch artery(ies).

Thus, in view of the above-discussed limitations and shortcomings, there remains a need in the art for the development of new endovascular grafting systems and methods which a) may be useable for endovascular grafting in regions of a blood vessel (e.g., aorta) from which branch blood vessels (e.g., carotid, innominate, subclavian, intercostal, superior mesenteric, celiac, renal or iliac arteries) extend, and/or b) may enable more aortic aneurysm patients to be considered as candidates for endovascular repair, and/or c) may otherwise advance the state of the art of endoluminal grafting to improve patient outcomes or lessen complications.

SUMMARY OF THE INVENTION

The present invention provides a system and method for edoluminal grafting of a blood vessel or other anatomical conduit, in a region where one or more branch anatomical conduit(s) (e.g., side branches, furcations, etc.) extend from the anatomical conduit.

In accordance with the present invention, there is provided an endoluminal grafting system which comprises:
  a) a primary graft which comprises;
    i) a first pliable tube (e.g., a tube formed of woven polyester, expanded polytetrafluoroethylene (ePTFE), or other biocompatible material) having a lumen extending longitudinally therethrough;
    ii) at least one branch opening (e.g., an aperture) formed in the first pliable tube;
    iii) a first connector (e.g., a groove, slot, depression, or other engageable surface) associated with (e.g., formed around or positioned adjacent to) the branch opening; and,
    iv) a primary graft anchoring device (e.g., a radially expandable stent, frame, series of rings, and/or adhesive, suture(s), staple(s), etc. for holding the graft in place) which is operative to hold the first pliable tube in a substantially fixed position within the lumen of the anatomical conduit, such that the branch opening is in alignment with the branch anatomical conduit; and,
  b) a branch graft which comprises;
    i) a second pliable tube having a proximal end, a distal end, and a lumen extending longitudinally therethrough;
    ii) a second connector (e.g., a ring, rib, ridge, protrusion or other engageable surface) associated with the proximal end of the second pliable tube, said second connector being engageable with said first connector to connect the proximal end of the second pliable tube to the first pliable tube such that fluid which flows through the lumen of the primary graft may pass through said branch opening and into the lumen branch graft.

In some applications, it will be desirable for the branch graft component of the above-summarized endoluminal grafting system to further include, or to be used in conjunction with,
    iii) a branch graft anchoring device (e.g., a radially expandable stent, frame, rings, and/or an adhesive, suture(s), staple(s), etc.) which is operative to hold at least the distal end of the branch graft in contact with the surrounding wall of the branch anatomical conduit.

Still further in accordance with the present invention, the above-summarized endoluminal grafting system may be implanted within the branched anatomical conduit by a method which comprises the following procedural steps:
  a) transluminally advancing the primary graft into the branched anatomical conduit;
  b) positioning the primary graft within the anatomical conduit such that the branch opening is aligned with the branch anatomical conduit;
  c) utilizing the primary graft anchoring device to anchor the primary graft within the anatomical conduit;
  d) transluminally advancing the branch graft into the lumen of the primary graft;
  e) passing the distal end of the branch graft through the branch opening and into the branch anatomical conduit; and,
  f) advancing the branch graft into the branch anatomical conduit until the second connector on the proximal end of the branch graft engages the first connector of the primary graft, thereby connecting the branch graft to the primary graft such that body fluid (e.g., blood) may flow from the lumen of the primary graft, through the branch opening, and through the lumen of the branch graft.

Still further in accordance with the present invention, the above summarized method may optionally include step of:
  g) utilizing a branch graft anchoring device to anchor at least the distal end of the branch graft to the surrounding wall of the branch anatomical conduit.

Still further in accordance with the present invention, there is also provided a method for implanting a modular, bifurcated endoluminal graft within a bifurcated anatomical conduit (i.e., a conduit having a main portion(e.g., aorta), a first furcation (e.g., right iliac) and a second furcation (e.g., left iliac), through a single access opening (e.g., cut down incision or percutaneous puncture site). This method generally comprises the steps of:
  a. providing a modular endoluminal graft which comprises i) a primary graft which is configured to be positioned in the main portion and first furcation of the anatomical conduit, and which has an opening formed therein, and ii) a branch graft which has a proximal end and a distal end and which is configured to be positioned in the second furcation of the anatomical conduit with its proximal end connected to the opening formed in the main graft;

b. forming an access opening which leads into the first furcation of the anatomical conduit;

c. advancing the bifurcated primary graft through the access opening and positioning the primary graft in the main portion and first furcation of the anatomical conduit;

d. advancing a curved guide catheter having an internal angle of curvature less than 90 degrees, into the main portion of the primary graft;

e. advancing a guidewire having a distal end, through the curved guide catheter, such that the distal end of the guidewire passes out of the curved guide catheter, through the opening formed in the primary graft, and into the second furcation of the anatomical conduit;

f. advancing a catheter having the branch graft mounted thereon, over the guidewire until the distal end of the branch graft extends into the second furcation of the anatomical conduit and the proximal end of the branch graft is connected to the opening formed in the primary graft; and, g. removing said guidewire and said catheter. In some applications of this method, an anchorable guidewire may be inserted in step e and the guidewire will then be anchored in the second furcation of the anatomical conduit, to prevent the guidewire form being inadvertently pulled out of the second furcation during the procedure. In procedure wherein such anchorable guidewire is used, the anchoring apparatus of the guidewire will be actuated prior to step f and will be deactuated prior to step g.

Still further in accordance with the invention, there is provided a new anchorable guidewire system which is useable in conjuntion with the above-sumarized method for implanting a bifurcated endoluminal graft and/or with various other medical or surgical procedures. This anchorable guidewire system comprises;

a) a balloon-anchorable guidewire which comprises:
   i) an elongate guidewire having a proximal end and a distal end;
   ii) a balloon formed on the guidewire at a first location;
   iii) a lumen which extends longitudinally through the guidewire from its proximal end to said balloon, said lumen being useable to pass inflation fluid into and out of said balloon; and, b) an inflation syringe/lumen-plugging apparatus which comprises:
   i) a syringe having a plunger and a barrel, said syringe being connectable to the proximal end of the guidewire such that when the plunger of said syringe is advanced in a first direction it will force inflation fluid through said lumen in the distal direction and into said balloon and, when said plunger is retracted in a second direction it will draw inflation fluid out of said balloon and through said lumen in the proximal direction; and,
   ii) a lumen-plugging member releasably mounted on the plunger of the syringe such that, when the plunger is advanced in the first direction to a predetermined point, the lumen-plugging memeber will become inserted into the guidewire lumen and is subsequently releasable from the plunger, said lumen-plugging member being thereby operative to prevent inflation fluid from escaping from said lumen when the syringe is removed.

In operation, the balloon-anchorable guidewire is inserted to its desired position and the inflation syringe/lumen-plugging apparatus is attached to its proximal end. The syringe plunger is then advanced in the distal direction, thereby inflating the balloon and anchoring the distal end of the guidewire at a desired position within the body. After the plunger has been advanced far enough to cause the lumen blocking member to be inserted into the proximal end of the guidewire lumen, the lumen blocking member is released (e.g., broken away or disconnected) from the plunger, and the lumen blocking member is allowed to remain inserted in proximal end of the lumen—acting as a plug to prevent fluid from escaping from the lumen. The syringe may then be detached and removed from the proximal end of the guidewire, and one or more catheters or other transluminal devices may be advanced and/or retracted over the proximal end of the guidewire. Thereafter, when it is desired to remove the guidewire, the exteriorized portion of the guidewire is cut (e.g., transected by a pair of standard scissors), thereby allowing the inflation fluid to leak from the balloon and out of the guidewire lumen. After the balloon has been deflated in this manner, the guidewire may be extracted and removed from the body.

Further aspects and details of the present invention will become apparent to those skilled in the art upon reading and understanding of the following detailed description and the drawings to which it refers.

BRIEF DESCRIPTION OF THE DRAWINGS

FIG. 1 is a schematic showing of a human body having an endoluminal grafting system of the present invention implanted to repair an abdominal aortic aneurism which involves the renal arteries.

FIG. 1a is an enlarged view of the perirenal aorta and endovascular grafting system shown in FIG. 1.

FIG. 1b is a partial longitudinal sectional view of an endoluminal grafting system of the present invention, showing a preferred means for connecting the proximal end of the branch graft to the primary graft.

FIG. 1c is an exploded view of the graft components shown in FIG. 1b.

FIG. 1d shows a first step in a preferred method for placing the branch graft(s) of an endoluminal grafting system of the present invention after the primary graft has been implanted.

FIG. 2 is a schematic showing of a human body having a the primary graft component of an endoluminal grafting system of the present invention implanted in the distal aorta and one iliac artery, to begin the repair of an infrarenal abdominal aortic aneurysm which has bilateral iliac involvement.

FIG. 2a is a view of the anneurysmic portion of the aorta in FIG. 2, showing a first step in a preferred method for placing an iliac branch graft in the remaining iliac artery to complete the implantation of the endoluminal grafting system of the present invention.

FIG. 2b is a view of the anneurysmic portion of the aorta in FIG. 2a, showing a second step in a preferred method for placing an iliac branch graft in the remaining iliac artery to complete the implantation of the endoluminal grafting system of the present invention.

FIG. 2c is a view of the anneurysmic portion of the aorta in FIG. 2b, following placement of an iliac branch graft in the remaining iliac artery and complete implantation of the endoluminal grafting system of the present invention.

FIG. 3 is a schematic showing of an infrarenal aortic aneurysm having bilateral iliac involvement and wherein the primary graft component of an endoluminal grafting system of the present invention has been implanted within the distal aorta and one iliac artery, to begin the repair of the aneurism, and a preferred balloon-anchorable guidewire of the present invention is being advanced into the contralateral iliac artery to facilitate placement of a branch graft within the contralateral iliac artery.

FIG. 3a shows the proximal end of the preferred anchorable guidewire of FIG. 3 connected to an inflation syringe/lumen plugging apparatus of the present invention, prior to inflation of the guidewire balloon.

FIG. 3b shows the proximal end of the preferred anchorable guidewire of FIG. 3 connected to an inflation syringe/lumen plugging apparatus of the present invention, following inflation of the guidewire balloon but before detachment of the inflation syringe.

FIG. 3c shows the proximal end of the balloon anchorable guidewire of FIG. 3 after inflation of the guidewire balloon and detachment of the inflation syringe, with the lumen-plugging apparatus having been separated from the inflation syringe and remaining in place within the proximal end of the guidewire lumen.

DETAILED DESCRIPTION OF THE PREFERRED EMBODIMENTS

Figure 1E:
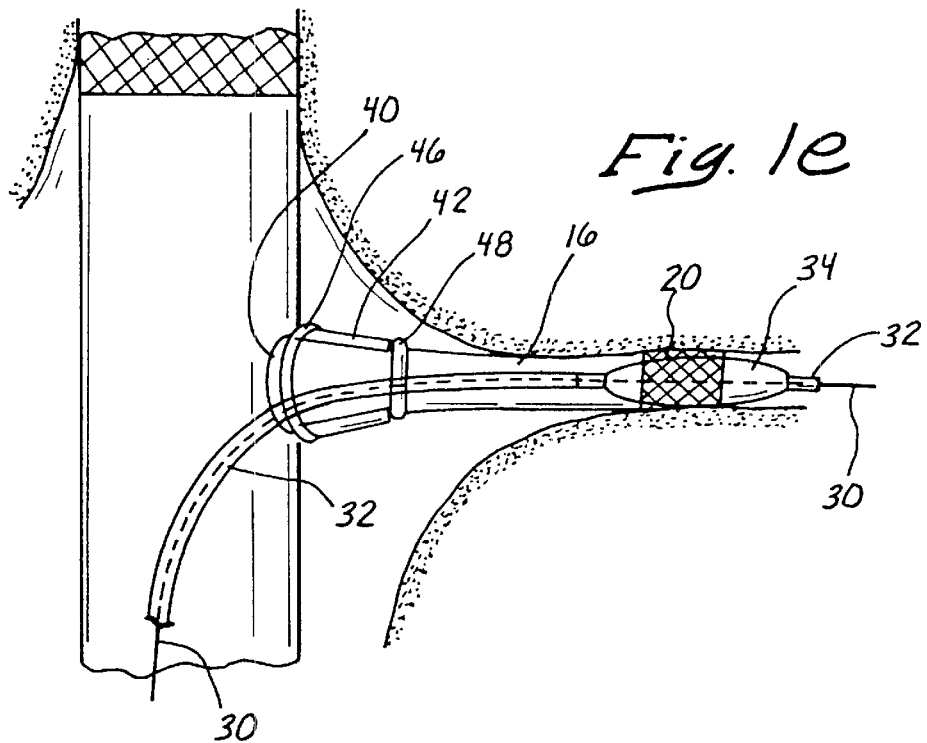
FIG. 1e shows a second step in a preferred method for placing the branch graft(s) of an endoluminal grafting system of the present invention after the primary graft has been implanted.

Referring now to the drawings, wherein the showings are for the purpose of illustrating presently preferred embodiments of the invention only and are not intended to limit the scope of the invention in any way.

The accompanying figures include various showings of human anatomical structures and such anatomical structures are labeled according to the following legend:

Aorta . . . A
Celiac Artery . . . CA
Femoral Artery . . . F
Heart . . . H
Iliac Arteries . . . IL ($IL_1$ and $IL_2$)
Kidneys . . . K
Renal Arteries . . . RA
Superior Mesenteric Artery . . . SMA A. General Structure and Function of Endoluminal Grafting Systems For Branched Anatomical Conduits As shown generally in FIGS. 1–2c, each preferred endoluminal grafting system 10 of the present invention generally comprises a primary graft 12 having at least one branch graft opening 14 formed therein, and at least one branch graft 16 which is advancable out of the branch graft opening 14 and into a branch anatomical conduit (e.g., a side branch or furcation of a blood vessel). A branch graft connector apparatus 17 is incorporated into the primary graft 12 and/or branch graft(s) 16 to connect the proximal end of the branch graft(s) 16 to the primary graft 12. One or more primary graft anchoring devices 18, such as radially expandable stent(s) or frame(s), is/are used to frictionally hold the primary graft 12 in a fixed position in the lumen of the primary anatomical conduit (e.g., aorta). Also, where necessary, one or more branch graft anchoring devices 20, such as radially expandable stent(s) or frame(s), may be used to frictionally hold at least the distal end of the branch graft(s) 16 in fixed position in the lumen(s) of the branch anatomical conduit(s) (e.g.,carotid, innominate, subclavian, intercostal, superior mesenteric, celiac, renal or iliac arteries). These primary graft anchoring device(s) 18 and branch graft anchoring device(s) 20 may be formed or incorporated into the body of the primary and branch grafts 12, 16 or, alternatively, they may be formed as separate structures (e.g., separate self-expanding or pressure-expandable stents) which are positioned within the lumens of the primary and branch grafts 12, 16, to accomplish the desired anchoring of the primary and branch grafts 12, 16, as shown.

Each branch graft opening 14 of the primary graft 12 is strategically placed, and preferably reinforced and marked for radiographic visualization, to facilitate precise alignment of each branch graft opening 14 with the particular branch anatomical conduit (e.g.,carotid, innominate, subclavian, intercostal, superior mesenteric, celiac, renal or iliac arteries) into which its branch graft 16 is to extend. The desire strategic placement of each branch graft opening 14 may be facilitated by custom-forming the branch graft opening(s) 14 in the primary graft 12, prior to implantation of the primary graft 12. Such pre-implantation, custom formation of the branch graft opening(s) 14 may be accomplished through the use of spiral computed tomography data of the vascular anatomy of the particular patient in whom the endovascular grafting system 10 is to be implanted. Notably, in applications where the primary graft 12 is being prepared for implantation in the thoracic or thoracoabdominal aorta, the branch graft openings 14 may be sized and positioned to align with relatively small side branch vessels (e.g.,carotid, innominate, subclavian, intercostal, superior mesenteric, celiac, or renal arteries) which, unlike the iliac bifurcation at the inferior end of the aorta, require a branch graft 16 be passable through such branch graft opening(s) 14 and into the smaller side branch vessel (e.g.,carotid, innominate, subclavian, intercostal, superior mesenteric, celiac, or renal arteries) at an angle of approximately 80–90 degrees relative to the axis of the aorta.

After the branch graft opening(s) 14 have been formed at the desired locations (and the appropriate portions of the bach graft connector 17 have been installed into the primary graft adjacent the branch graft opening(s) 14), the primary graft 12 is inserted via an introducer into the femoral artery, and advanced under radiographic guidance into the site (e.g., the aneurysmic segment of vessel) where the primary graft 12 is to be implanted. This insertion of the primary graft 12 (and any primary graft anchoring device(s) 18 which are formed separately from the graft 12) may be facilitated by mounting the primary graft 12 (and any such separate graft anchoring devices 18) on a balloon catheter or other suitable delivery catheter capable of carrying the primary graft (and any separate graft anchoring device(s) 18) to the intended site of implantation. The primary graft 12 and any separate primary graft anchoring device 18 is/are then radially expanded or otherwise deployed such that the primary graft becomes anchored in a substantially fixed position within the primary anatomical conduit (e.g., aorta A). In applications wherein the endoluminal grafting system 10 is being used to repair an aneurysm, the hemodynamic pressure within the aneurysm sac (i.e., the space within the aneurysm but outside the primary graft 12), as well as the hemodynamic pressure within the branch anatomical conduit(s)

which emanate from the aneurysmic segment of vessel, will be substantially unaffected by the initial placement of the primary graft 12 because, until such time as the branch graft(s) 14 have been introduced, blood will continue to flow out of the branch graft opening(s) 14 of the primary graft 12.

After the primary graft 12 has been positioned and anchored within the primary anatomical conduit (e.g., aorta A), a guidewire 30 may be transluminally advanced through the lumen of the primary graft 12, out of a branch opening 14 and into the branch anatomical conduit (e.g., . In some applications, a guide catheter may be introduced into the lumen of the primary graft 12 to facilitate passage of the guidewire 30 out of the desired branch graft opening 14.

A branch graft 16 is then mounted on a balloon catheter 32, and the distal end of the branch graft may be drawn taught about the catheter balloon 34 by a purse string suture 36 (e.g., 7.0 polypropylene suture material). The balloon catheter 32 having the branch graft 16 mounted thereon is then advanced over the guidewire 30 until the proximal end of the branch graft 16 becomes connected to the branch graft opening 14 of the primary graft 12 by way of the branch graft connector apparatus 18. Thereafter, the catheter balloon 34 is inflated, causing the purse string suture 36 to break and the distal end of the branch graft 16 to radially expand into contact with the surrounding wall of the branch anatomical conduit.

Figure 1F:
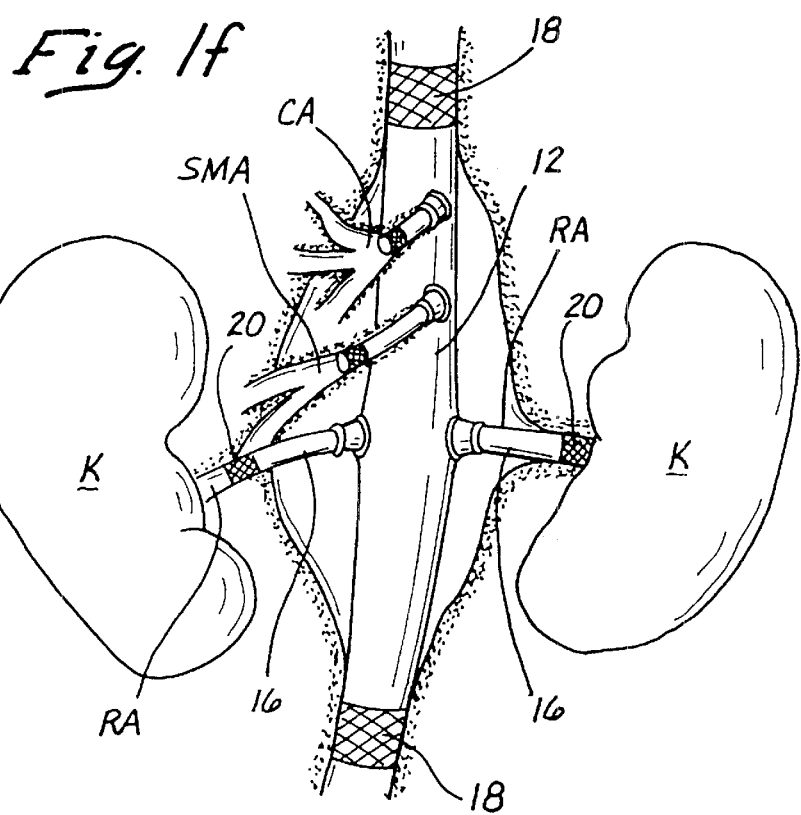
FIG. 1f is a schematic showing of a portion of a human aorta having an endoluminal grafting system of the present invention implanted to repair a thoracoabdominal aortic aneurysm which involves the renal, superior mesenteric and celiac arteries.

A presently preferred branch graft connector apparatus 17 is shown in detail in FIGS. 1b–1e. The components of this branch graft connector apparatus 17 associated with the primary graft 12 comprise: a first rigid or semirigid ring 40 which surrounds the branch graft opening 14, and a rigid or semirigid frustoconical member 42 which extends outwardly from the first ring member 40, as shown in FIG. 1b. The components of this branch graft connector apparatus associated with the branch graft 16 comprise a rigid or semirigid, tapered proximal portion 44, a second rigid or semirigid ring member 46 on the proximal end of the tapered proximal portion 44, and a third rigid or semirigid ring member 48 formed about the tapered proximal portion 44 at a spaced distance from the second ring member. The distance between the outer surface OS of the second ring member 46 and the inner surface IS of the third ring member 48 is substantially the same as the distance between the inner surface IS of the first ring member 40 and the distal end DE of the frustoconical member 42. In this manner, as the branch graft 12 is advanced, distal end first, out of the branch graft opening 14 it will reach a point of maximum advancement whereat the inner surface IS of the first ring member 40 will abut against the outer surface OS of the second ring member 46, and the distal end DE of the frustoconical member 42 will abut against the inner surface IS of the third ring member 48. This will create a substantially fluid-tight seal between the proximal end of the branch graft 16 and the body of the primary graft 12. Additionally, this may form a snap-fit connection which will prevent the branch graft 14 from slipping or undergoing inadvertent retraction back into the lumen of the primary graft 12.

It will be appreciated that an audible or tactilely discernible indicator (e.g., a"snap") may occur as the separate components of the branch graft connector 17 come together, thereby indicating to the operator that the desired engagement and sealing of the proximal end of the branch graft 16 to the primary graft 12 has been accomplished. Also, the ring members 40, 46, and 48 may be formed of radiographically visible material to enable the operator to radiographically confirm that the branch graft 16 has been firmly connected to and engaged with the primary graft 12. Additionally, it is to be appreciated that the branch graft connector 17 need not necessarily be a mechanical connector apparatus as shown in the drawings, but may alternatively comprise any mechanical, electromagnetic, frictional, or chemical (e.g., adhesive, coupling, or fusing agent) capable of joining the proximal end of the branch graft 16 to the primary graft 12 in substantially fluid-tight sealing contact.

B. A Specific Endoluminal Grafting System and Method for Repair of Aortic Aneurysms Having Iliac Involvement FIGS. 2–3c are specifically directed to embodiments of the endovascular grafting system 10a for the repair of aneurysms of the infrarenal aorta A which extend into the iliac arteries IL. This embodiment of the endoluminal grafting system 10a differs from the above-described embodiment 10 in the primary graft 21a has a bifurcation 64 formed therein, and includes a main aortic portion 60 and one iliac portion 62. The branch graft opening 14 of this embodiment 10a is formed on one side of the bifurcation 64 to facilitate passage of the branch graft 14 into the iliac artery IA which is opposite the iliac artery IA into which the iliac portion 62 of the primary graft 12a has been positioned. Also, in the primary graft component 12a of this embodiment 10a the primary graft anchoring devices 18 are located at the superior end of the main portion 60 and the inferior end of the iliac portion 62, as shown in FIG. 2a.

The present invention also includes a novel method for implanting a bifurcated endoluminal graft, such as the embodiment 10a shown in FIGS. 2–2c, through a single access opening (e.g., percutaneous puncture site or cut down incision). It is to be appreciated, however, that this method may also be useable for implantation of various other bifurcated endoluminal grafts, and the applicability of this method is not necessarily limited to the particular bifurcated endoluminal grafting system 10a of the present invention.

With reference to the step-wise showings of FIGS. 2a–2c, the preferred method comprises the steps of:

1. Forming an access opening 66 into one of the femoral arteries F, and advancing a guidewire 30 through such access opening 66, through the contiguous iliac artery $IL_1$, and into the aorta A;
2. Advancing the bifurcated primary graft 12a over the guidewire 30, and positioning the primary graft 12a in the aorta A and first iliac artery $IL_1$ such that its branch graft opening 14a is directed toward the other iliac artery $IA_2$, as shown in FIG. 2a;
3. Causing the primary graft anchoring device 18 to hold at least the superior end of the aortic portion 60 of the primary graft 12a in the aorta A, and the inferior end of the iliac portion 62 of the primary graft 12a in the first iliac artery $IA_1$;
4. Advancing a curved guide catheter 68, having an angle of curvature AC less than 90 degrees, into the lumen of the aortic portion 60 of the primary graft 21a;
5. Advancing the guidewire 30 through the guide catheter 68, such that the distal end of the guidewire 30 passes out of the distal end of the curved guide catheter 68 and into the other iliac artery $IA_2$;
6. Advancing the balloon catheter 32 having the branch graft 14 mounted thereon, over the guidewire 30 as shown in FIG. 2b, until the branch graft connector apparatus 17 becomes connected, thereby forming a fluid tight sealing connection between the proximal end of the branch graft 14 and the primary graft 12a;
7. Inflating the balloon 34 of the balloon catheter 32 to break the purse string stitch 36 and to radially expand the branch graft anchoring device 20 (if present);
8. Deflating the catheter balloon 32; and, 9. Removing the guidewire 30 and balloon catheter 32 from the body.

Thus, by the above described steps of the method of the present invention, an endoluminal grafting system 10a may be implanted in a bifurcated anatomical conduit, with only one (1) access opening (e.g., puncture site or incision) formed in the body.

In at least some applications of the method it may be desirable to anchor the distal end of the guidewire 30 within the contralateral iliac artery $IL_2$ to prevent the guidewire from becoming displaced (i.e., pulled out of the contralateral iliac artery $IL_2$ during the advancement of the branch graft 14. Various types of anchorable (e.g., balloon-anchorable or tip-deflectable) guidewires could be useable in (or modifiable for use in) this procedure. Examples of such previously known anchorable guidewires include those described in U.S. Pat. No. 5,167,239 (Cohen et al.); U.S. Pat. No. 5,480,362 (Hammerslag et al.) and U.S. Pat. No. 5,497,782 Fugoso).

Additionally, the present invention includes a new anchorable guidewire system 78 as shown in FIGS. 3–3c and described more fully herebelow.

C. A Preferred Anchorable Guidewire System

FIGS. 3–3c show a preferred anchorable guidewire system 78 of the present invention. This anchorable guidewire system 78 is useable in the performance of the above-described method for repairing aneurysms of the aorta which have iliac involvement. Additionally, this anchorable guidewire system 78 may have numerous other applications in the performance of various medical procedures in interventional cardiology, interventional radiology, gastroenterology, and surgery.

The preferred anchorable guidewire system 78 comprises a pliable guidewire 80 and an inflation syringe/lumen plugging apparatus 82. The guidewire 80 has a balloon 83, such as a soft shape-conformable balloon (e.g. latex), formed about the distal portion of the guidewire 80 and a balloon inflation/deflation lumen 81 extending longitudinally through the guidewire 80 to permit balloon inflation fluid (e.g., saline, $CO_2$, room air) to be passed into and out of the balloon. The inflation syringe/lumen plugging apparatus 82 comprises, a syringe having a generally cylindrical barrel 85 and a plunger 86 which is in fluid-tight contact with the barrel 85. The plunger 86 slides longitudinally back and forth within the barrel 85 to alternately a) draw fluid into the barrel 85, and b)expel fluid out of the barrel 85. A lumen-plugging apparatus 84 is attached to the distal face of the plunger 86 and protrudes distally therefrom, as shown. This lumen-plugging apparatus is detachable from the plunger 86 by any acceptable means, such as a breakable attachment which will be severed when the plunger 86 is rotated while the lumen-plugging apparatus 84 is held in a fixed non-rotating position. To facilitate this, the lumen plugging apparatus 84 may, when inserted into the proximal end of the guidewire lumen 81, engage the surrounding wall of the guidewire lumen 81 tightly enough to prevent the lumen plugging apparatus 84 from rotating when the plunger 86 is rotated. In this rotation-preventing surface texturing, such as a system of longitudinal ribs or corresponding longitudinal ribs & grooves (not shown), may be formed on the outer surface of the lumen plugging apparatus 84 and/or the surrounding wall of the guidewire lumen 81 such that rotation of the lumen plugging apparatus 84 will be frictionally prevented or deterred.

As shown in FIG. 3a the inflation syringe/lumen plugging apparatus 82 is initially attached to the guidewire 80, with its plunger 86 in a withdrawn position, and with the proximal end of the guidewire inserted into the barrel 85 of the syringe 82. In this manner, inflation fluid is contained within the barrel 85 for use in inflating the balloon 83, when desired.

Thereafter, as shown in FIG. 3b, when it is desired to inflate the balloon 83, the plunger 86 of the syringe 82 is advanced in the distal direction, thereby forcing inflation fluid out of the barrel 85, through the guidewire lumen 81, and into the balloon 83. This results in inflation of the balloon 83 and anchoring of the distal end of the guidewire 80. This also causes the lumen plugging apparatus 84 on the distal face of the plunger 86 to be forced into the proximal end of the guidewire lumen 81, thereby plugging the lumen 81 to prevent the balloon inflation fluid form escaping from the balloon. Also, in the particular embodiment shown in the drawings, this will also cause the lumen plugging apparatus 84 to be non-rotatably engaged to the guidewaire 80.

Thereafter, when it is desired to pass the balloon catheter 32 or other device over the proximal end of the guidewire 80, the plunger 86 of the syringe 82 is rotated. Such rotation of the plunger 86 causes the lumen-plugging apparatus 84 to break away from, or separate from, the plunger 86. This allows the syringe 82 to be removed, as shown in FIG. 3c, while the lumen plugging apparatus remains inserted within the proximal end of the guidewire lumen 81 to prevent the inflation fluid from escaping from the guidewire balloon 83.

Subsequently, when it is desired to deflate the balloon 83 to allow the guidewire to be extracted, the operator may simply cut the guidewire 80 at a location distal to the lumen plugging apparatus 84, thereby allowing the balloon inflation fluid to escape from the lumen 81 and causing the balloon 83 to deflate.

It will be appreciated that, although the invention has been described hereabove with reference to certain presently preferred embodiments or examples shown in the drawings, various modifications could be made to those presently preferred embodiments or examples without departing from the intended spirit and scope of the invention. Accordingly, it is intended that all such modifications to the above-described preferred embodiments or examples be included within the scope of the following claims.

What is claimed is:

1. A method of endoluminal grafting of an anatomical conduit which has at least one branch anatomical conduit extending therefrom, said method comprising the steps of:

a) providing an endovascular grafting system which comprises:

i) a tubular primary graft, said primary graft having a lumen extending longitudinally therethrough, a branch graft opening formed at a first location therein; a first connector member formed adjacent said branch graft opening; and a primary graft anchoring component which operates to hold the primary graft in a substantially fixed position within the lumen of the anatomical conduit; and, ii) a tubular branch graft, said branch graft having a proximal end, a distal end, and a lumen extending longitudinally therethrough, a second connector member being formed on the proximal end of the branch graft, said second connector member being configured to engage the first connector member formed on the primary graft, to thereby form a substantially fluid-tight connection between the proximal end of the branch graft and the primary graft;

b) placing the primary graft in a collapsed configuration, and passing the primary raft into the anatomical conduit;

c) expanding the primary graft from its collapsed to an operative configuration wherein the primary graft abuts against the surrounding wall of the anatomical conduit;

d) utilizing the primary graft anchoring component to hold the primary graft in fixed position within the anatomical conduit, with the branch graft opening being in alignment with the branch anatomical conduit;

e) advancing a guidewire through the lumen of the primary graft, through the branch graft opening and into the branch anatomical conduit;

f) attaching the distal end of the branch graft to a tubular delivery catheter;

g) advancing the delivery catheter over the guidewire such that the distal end of the branch graft is carried into the branch anatomical conduit, and the second connector member on the branch graft is brought into engagement with the first connector member on the primary graft, thereby forming a connection between the proximal end of the branch graft and the primary graft.

2. The method of claim 1 wherein the delivery catheter used in step f has a balloon formed thereon, and wherein the distal end of the graft is secured about the balloon by way of a breakable member, such breakable member being breakable upon inflation of the balloon.

3. The method of claim 2 wherein the method further comprises the step of:

h) inflating the balloon so as to break the breakable member, thereby allowing the distal end of the branch graft to expand into contact with the wall of the branch anatomical conduit.

4. The method of claim 3 further comprising the step of:

i) advancing a separate branch graft anchoring device into the branch graft lumen, and causing the anchoring device to hold at least the distal end of the branch graft in contact with the wall of the branch anatomical conduit.

5. The method of claim 4 wherein the branch graft anchoring device is a radially expandable stent, said stent being positioned within the lumen of the branch graft, adjacent its distal end.

6. The method of claim 2 wherein the breakable member is a segment of suture thread.

7. The method of claim 2 wherein the breakable member is attached to the catheter such that, after the breakable member has been broken, it may be extracted and removed from the body along with the catheter.

8. A method for endoluminal grafting of a bifurcated anatomical conduit having a main portion, a first furcation, and a second furcation, said method comprising the steps of:

a. providing a modular endoluminal graft which comprises
   i) a primary graft which is configured to be positioned in the main portion and first furcation of the anatomical conduit, and which has been formed therein, and
   ii) a branch graft which has a proximal end and a distal end and which is configured to be positioned in the second furcation of the anatomical conduit with its proximal end connected to the opening formed in the primary graft;

b. forming an access opening which leads into the first furcation of the anatomical conduit;

c. advancing the bifurcated primary graft through the access opening and positioning the primary graft in the main portion and first furcation of the anatomical conduit;

d. advancing a curved guide catheter having an internal angle of curvature less than 90 degrees, into the main portion of the primary graft;

e. advancing a guidewire having a distal end, through the curved guide catheter, such that the distal end of the guidewire passes out of the curved guide catheter, through the opening formed in the primary graft, and into the second furcation of the anatomical conduit;

f. advancing a catheter having the branch graft mounted thereon, over the guidewire until the distal end of the branch graft extends into the second furcation of the anatomical conduit and the proximal end of the branch graft is connected to the opening formed in the primary graft; and g. removing said guidewire and said catheter.

* * * * *